United States Patent [19]

Meilland, deceased

[11] Patent Number: Plant 6,810

[45] Date of Patent: May 23, 1989

[54] ROSE PLANT — MEIPONAL VARIETY

[75] Inventor: Marie-Louise Meilland, deceased, late of Antibes, France, by Jean-Pierre le Naour, legal representative

[73] Assignee: The Conard-Pyle Company, West Grove, Pa.

[21] Appl. No.: 145,394

[22] Filed: Jan. 19, 1988

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which forms abundantly and continuously highly attractive semi-double blossoms. The blossoms are light ochre yellow on the upper surface and pale buttercup yellow on the under surface. The plant is well suited for pot forcing and forms attractive ornamentation when grown as a flowering pot plant either indoors or outdoors.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the Meihand variety (non-patented) by the Moulin Rouge variety (U.S. Plant Pat. No. 1,298). The male parent (i.e., the pollen parent) of the new variety was the product of the pollination of the Meialfi variety (non-patented) by the Meikim variety (non-patented). The parentage of the new variety can be summarized as follows:

[Meihand × Moulin Rouge] × ]Meialfi × Meikim].

The seeds resulting from the above pollination were sown and 197 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive semi-double blossoms which are light ochre yellow on the upper surface and pale buttercup yellow on the under surface,
(b) exhibits a bushy growth habit, and
(c) is well suited for pot forcing.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meiponal variety, and is being marketed by The Conard-Pyle Company under the Sunny Sunblaze trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during June while growing on their own roots outdoors at Cannet-des-Maures, Var, France.

DETAILED DESCRIPTION

Figures 1, 2, 3, 4, 5, 6, 7, 8, 9, 10, 11, 12, 13, 14, 15:
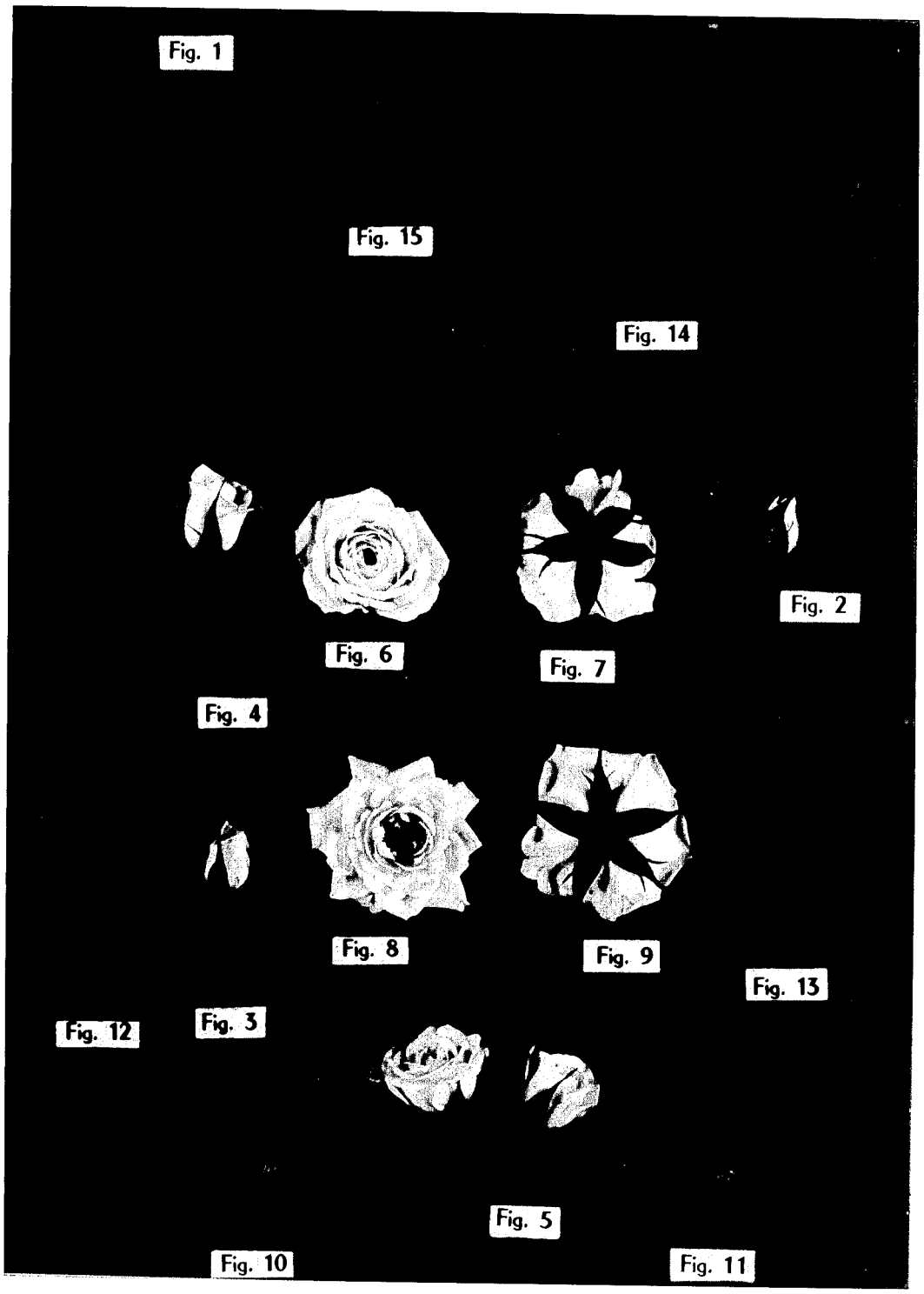
FIG. 1 illustrates specimens of two young shoots.
FIG. 2 illustrates specimens of two floral buds before the opening of the sepals.
FIG. 3 illustrates a specimen of a floral bud at the opening of the sepals.
FIG. 4 illustrates a specimen of a floral bud at the opening of the petals.
FIG. 5 illustrates specimens of two flowers in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils (sepals removed)
FIG. 11 illustrates a specimen of a floral receptacle showing the arrangement of the pistils (sepals and stamens removed)
FIG. 12 illustrates a specimen of a flowering stem.
FIG. 13 illustrates a specimen of a main branch.
FIG. 14 illustrates specimens of leaves with three leaflets with the upper surface being shown on the right and the under surface being shown on the left.
FIG. 15 illustrates specimens of leaves with five leaflets with the upper surface being shown on the top and the under surface being shown on the bottom.

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety during June while growing on their own roots outdoors at Cannet-des-Maures, Var, France.

Class: Miniature.

Plant:

*Height.*—Approximately 25 to 30 cm. on average.

*Habit.*—Bushy.

Branches:

*Color.*—Young stems: light green, Yellow-Green Group 144B. Adult wood: light green, Yellow-Green Group 146B.

Leaves:

*Petioles.*—Upper surface: grooved, very light green on young foliage and light green on adult foliage with glandular edges. Under surface: light green with hooked thorns.

*Stipules.*—Adnate, pectinate, narrow and linear.

*Leaflets.*—Number: 3, 5 (most often). Shape: elliptic. Serration: simple and regular. Texture: firm. General appearance: dark green foliage which is non-glossy and of average density. Color (young foliage): Upper surface: lettuce green, Yellow-Green Group 144A. Under surface: light green, Yellow-Green Group 144B. Color (adult foliage): Upper surface: dark green, Yellow-Green Group 147A. Under surface: dark green, Yellow-Green Group 147B.

Inflorescence:

*Number of flowers.*—Approximately 1 to 5 per stem.

*Peduncle.*—Straight, rigid, it bears many glandular aciculas, its length is approximately 5 cm. on average.

*Sepals.*—Upper surface: tomentose, and greenish in coloration. Under surface: light green, smooth, the outside sepals have edges which are more or less glandular and appendiculated.

*Buds.*—Shape: slightly globular. Length: approximately 1.5 cm. on average. Size: average. Color upon opening: Upper surface: light ochre yellow, Yellow-Orange Group 20C. Under surface: pale buttercup yellow, Yellow-Orange Group 16D.

*Flower.*—Form: as a cup. Diameter: approximately 5.5 cm. on average. Color (when opening begins): Upper surface: light ochre yellow, Yellow-Orange Group 20C. Under surface: pale buttercup yellow, Yellow-Orange Group 16D. Color (when blooming): Upper surface: light ochre yellow, Yellow-Orange Group 20C. Under surface: pale buttercup yellow, Yellow-Orange Group 16D. Color (at end of opening): Upper surface: light ochre yellow, Yellow-Orange Group 20C, and blending to Yellow-Orange Group 20D on the outside petals. Under surface: pale buttercup yellow, Yellow-Orange Group 16D. Fragrance: none. Lasting quality: long. Petal number: approximately 35 on average. Petal form: oval, lightly serrated with an obtuse base, the outside petals sometimes have a greenish median line, and the central petals often are not whole. Petal texture: firm. Petal drop: good. Anthers: normal, ochre yellow. Stamen number: approximately 65 on average. Filaments: straw colored and of irregular heights. Pistil number: approximately 73 on average. Stigmas: normal, yellowish in coloration. Styles: free, fuchsine, tomentose, sometimes twisted, of irregular heights. Receptacle: light green at the dehiscence of the anthers and in longitudinal section is narrow and funnel shaped.

Development:

*Vegetation.*—Vigorous.

*Blooming.*—Abundant and continuous.

*Aptitude to bear fruit.*—Average.

*Resistance to frost.*—Good.

*Resistance to disease.*—Good.

It is claimed:

1. A new and distinct variety of Miniature rose plant characterized by the following combination of characteristics:

(a) forms in abundance on a continuous basis attractive semi-double blossoms which are light ochre yellow on the upper surface and pale buttercup yellow on the under surface, (b) exhibits a bushy growth habit, and (c) is well suited for pot forcing;

substantially as herein shown and described, together with the parts thereof.

* * * * *